(12) United States Patent
Won et al.

(10) Patent No.: US 12,734,262 B2
(45) Date of Patent: Sep. 15, 2026

(54) IN-VEHICLE STERILIZATION SYSTEM

(71) Applicant: HYUNDAI MOBIS Co., Ltd., Seoul (KR)

(72) Inventors: Hyung Jin Won, Yongin-si (KR); Seung Jae Kim, Yongin-si (KR); Jong Joo Kang, Gunpo-si (KR)

(73) Assignee: Hyundai Mobis Co., Ltd., Seoul (KR)

( * ) Notice: Subject to any disclaimer, the term of this patent is extended or adjusted under 35 U.S.C. 154(b) by 578 days.

(21) Appl. No.: 17/982,657

(22) Filed: Nov. 8, 2022

(65) Prior Publication Data

US 2024/0148921 A1 May 9, 2024

(51) Int. Cl.
*A61L 2/10* (2026.01)
*A61L 2/24* (2006.01)
*A61L 103/75* (2026.01)

(52) U.S. Cl.
CPC .................................... *A61L 2/10* (2013.01); *A61L 2/24* (2013.01); *A61L 2103/75* (2026.01); *A61L 2202/14* (2013.01); *A61L 2202/16* (2013.01)

(58) Field of Classification Search
CPC ........................................................ A61L 2/10
See application file for complete search history.

(56) References Cited

U.S. PATENT DOCUMENTS

2021/0403294 A1* 12/2021 Szczepkowski ...... B66C 13/085

FOREIGN PATENT DOCUMENTS

| | | | |
|---|---|---|---|
| CN | 213502054 | U | 6/2021 |
| CN | 113752792 | A | 12/2021 |
| KR | 10-2009-0036703 | A | 4/2009 |
| KR | 10-2022-0072651 | A | 6/2022 |
| KR | 10-2422985 | B1 | 7/2022 |

OTHER PUBLICATIONS

English Machine Translation. Shen CN 113752792 (Year: 2021).*
Partial European search report issued on Apr. 12, 2023, in counterpart European Patent Application No. 22206425.5 (12 pages in English).

* cited by examiner

*Primary Examiner* — Donald R Spamer
(74) *Attorney, Agent, or Firm* — NSIP Law

(57) ABSTRACT

Disclosed is an in-vehicle sterilization system. The system includes a sterilizer that includes one or more ultraviolet (UV) light-emitting diodes (LEDs). The system also includes processors that determine a time point at which the sterilizer is to be operated, and control operation of the sterilizer according to a result of the determination.

13 Claims, 12 Drawing Sheets

IN-VEHICLE STERILIZATION SYSTEM

BACKGROUND

1. Field

The present disclosure relates to an in-vehicle sterilization system configured to sterilize the interior of a vehicle using ultraviolet light-emitting diodes (UV LEDs) in any conditions.

Vehicles are known to be provided with lamps that provide normal visible light in a variety of locations to illuminate the interior of the vehicle at night. To sterilize the interior of a vehicle, a driver may sterilize the interior of the vehicle by irradiating the interior of the vehicle with UV radiation generated by an independent sterilization system.

Systems for sterilizing household items have been introduced in the form of independent systems using UV LEDs. These related-art systems include systems for sterilizing household items using UV LEDs are a toothbrush sterilizer, a baby bottle sterilizer, and the like that sterilize microorganisms and viruses in household items that are generally taken into the mouth.

There are three types of UV radiation, long wavelength UV radiation (UV-A), medium wavelength UV radiation (UV-B), and short wavelength UV radiation (UV-C). UV sterilizers generally use short wavelength UV radiation and have 99.9% sterilization power when UV radiation is only projected for 20 seconds. However, UV radiation may be harmful when directly projected to human bodies.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an in-vehicle sterilization system includes a sterilizer that includes one or more ultraviolet (UV) light-emitting diodes (LEDs). The system also includes processors that determine a time point at which the sterilizer is to be operated, and control operation of the sterilizer according to a result of the determination.

The processors may determine whether or not information regarding an operation time of the sterilizer is stored and, when the operation time is reached, control operation of the sterilizer for the operation time.

The in-vehicle sterilization system may further include a communication system communicating with a remote control terminal, wherein, when a remote start signal and a remote sterilization request signal are received through the communication system, the processors control operation of the sterilizer for a predetermined operation time.

When unlocking of a door is detected during the predetermined operation time, the processors may stop the sterilizer.

The sterilizer may include multiple sterilizing components. When a sterilization request is received from the remote control terminal, the driving processors may operate the sterilizer, according to a setting a vehicle itself, in one of a quick sterilization mode in which some of the plurality of sterilizing components operate, and an entirety sterilization mode in which all of the plurality of sterilizing components operate.

The in-vehicle sterilization system may further include sensors that detect whether a child or a pet is present inside the vehicle. When the sterilization request is received from the remote control terminal, the processors may detect whether a child or a pet is present inside the vehicle and, when neither a child nor a pet is present inside the vehicle, operate the sterilizer.

The sterilizing part may include a housing including a longitudinal channel provided on a front portion of the housing and having an open front portion and a UV mounting panel provided below a rear portion of the channel and having a space for accommodating the UV LEDs, a luminescent fiber disposed in the channel of the housing to project RGB light under control, the UV LEDs mounted on a lower portion of the UV mounting panel to generate UV radiation under control, and an upper garnish configured to cover an open portion of the channel such that the luminescent fiber disposed in the channel is not released outward.

The UV LEDs may be a plurality of UV LEDs arranged along the UV mounting panel.

The in-vehicle sterilization system may further include a UV reflector disposed below the UV mounting panel and at a predetermined distance from the housing such that the UV radiation generated by the UV LEDs is projected outward.

The UV reflector may have a predetermined curvature so that the UV radiation generated by the UV LEDs is uniformly projected.

The in-vehicle sterilization system may further include a UV transparent film between the UV reflector and the housing.

The processors may determine an operation mode based on a time point and a position at which a request is received and a driver use pattern.

The sterilizer may include a plurality of sterilizing components disposed on one or more of a mood lamp, a door lamp, and a room lamp.

The sterilizer may be disposed on an air vent of an air conditioning system provided in a ceiling of a vehicle.

Information regarding a result of the operation of the sterilizer may be transmitted to and displayed on an audio, video, and navigation (AVN) system or a remote control terminal.

Other features and aspects will be apparent from the following detailed description, the drawings, and the claims.

BRIEF DESCRIPTION OF THE DRAWINGS

FIG. 9 is a reference view illustrating a ceiling air vent disposed in the upper portion of the interior of a vehicle, with the sterilizing part illustrated in FIG. 1 being disposed on the ceiling air vent, and objects to be sterilized by the sterilizing part.

FIG. 10 is a reference view illustrating a state in which the interior of a vehicle is sterilized by the sterilizing part illustrated in FIG. 9.

Figure 1:
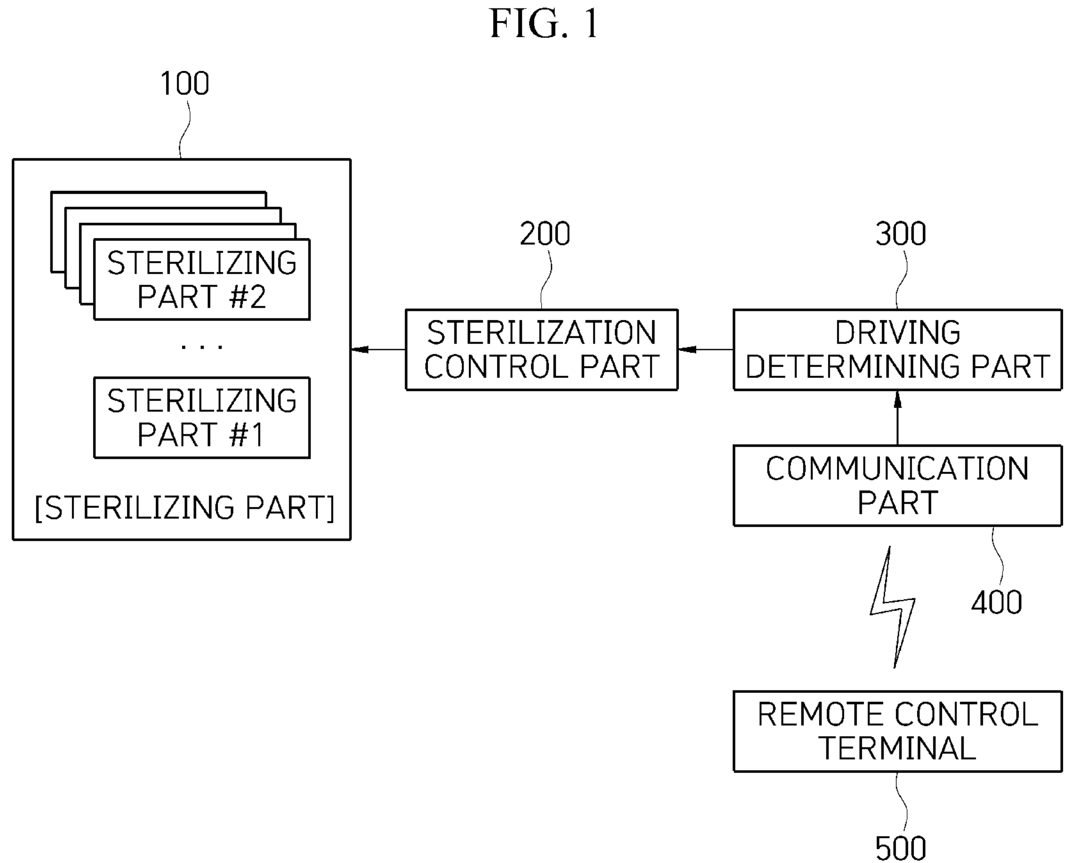
FIG. 1 is a block diagram illustrating a configuration of an in-vehicle sterilization system according to an embodiment of the present disclosure.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order.

The features described herein may be embodied in different forms and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Advantages and features of the present disclosure and methods of achieving the advantages and features will be clear with reference to embodiments described in detail below together with the accompanying drawings. However, the present disclosure is not limited to the embodiments disclosed herein but will be implemented in various forms. The embodiments of the present disclosure are provided so that the present disclosure is adequately disclosed, and a person with ordinary skill in the art can fully understand the scope of the present disclosure. Meanwhile, the terms used in the present specification are for explaining the embodiments, not for limiting the present disclosure.

Terms, such as first, second, A, B, (a), (b) or the like, may be used herein to describe components. Each of these terminologies is not used to define an essence, order or sequence of a corresponding component but used merely to distinguish the corresponding component from other component(s). For example, a first component may be referred to as a second component, and similarly the second component may also be referred to as the first component.

Throughout the specification, when a component is described as being "connected to," or "coupled to" another component, it may be directly "connected to," or "coupled to" the other component, or there may be one or more other components intervening therebetween. In contrast, when an element is described as being "directly connected to," or "directly coupled to" another element, there can be no other elements intervening therebetween.

The use of the term "up" or "upward" herein is meant to refer to a direction wherein a corresponding vehicle includes wheels on a lower portion of the vehicle compared to a roof of the vehicle in an upper portion of the vehicle.

The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

FIG. 1 is a block diagram illustrating a configuration of an in-vehicle sterilization system according to an embodiment of the present disclosure.

Referring to FIG. 1, the in-vehicle sterilization system according to an embodiment of the present disclosure may include at least one sterilizing part (for example, a sterilizer) 100, a driving determining part 300, a sterilization control part 200, a communication part 400, and a remote control terminal 500. The driving determining part 300, and sterilization control part 200 may be part of the electronic control unit (ECU) or respective ECUs each having one or more processors configured to perform the processes as detailed herein below, including determining a time point at which the sterilizing part 100. Communication part 400 may include, for example, a transceiver configured to receive communications. Remote control terminal 500 may be a user device, such as, for example, a mobile device.

Figure 9:
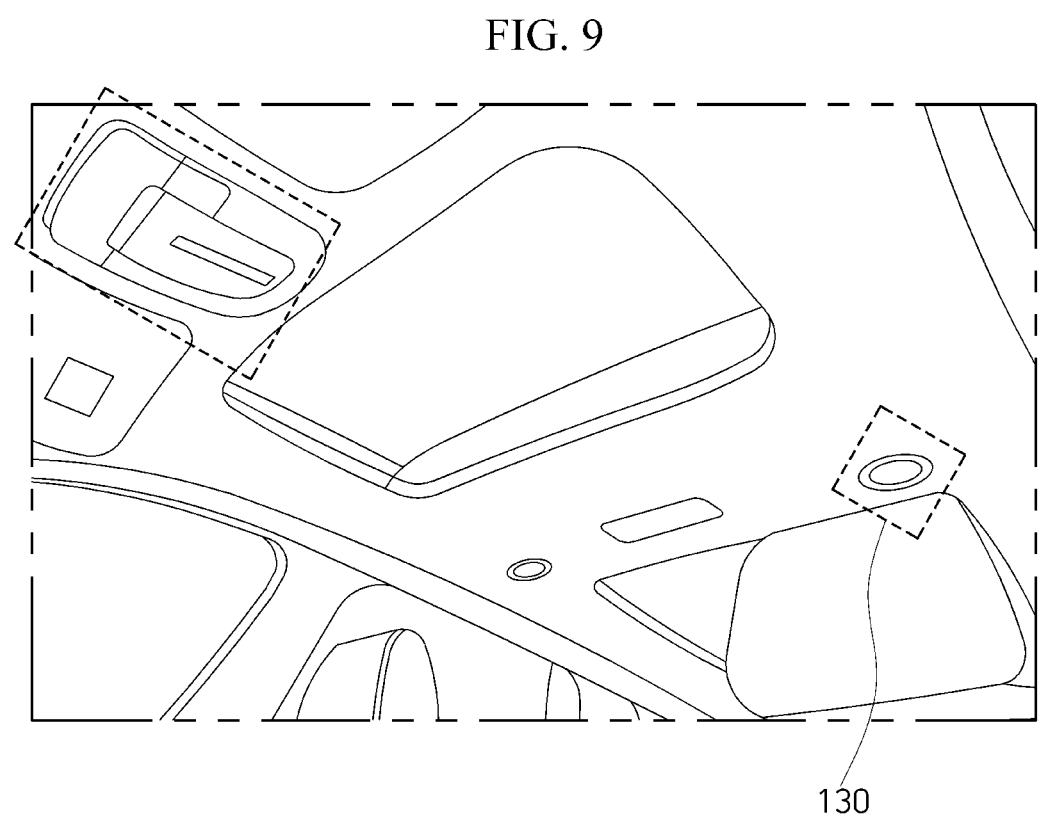
Figure 10:
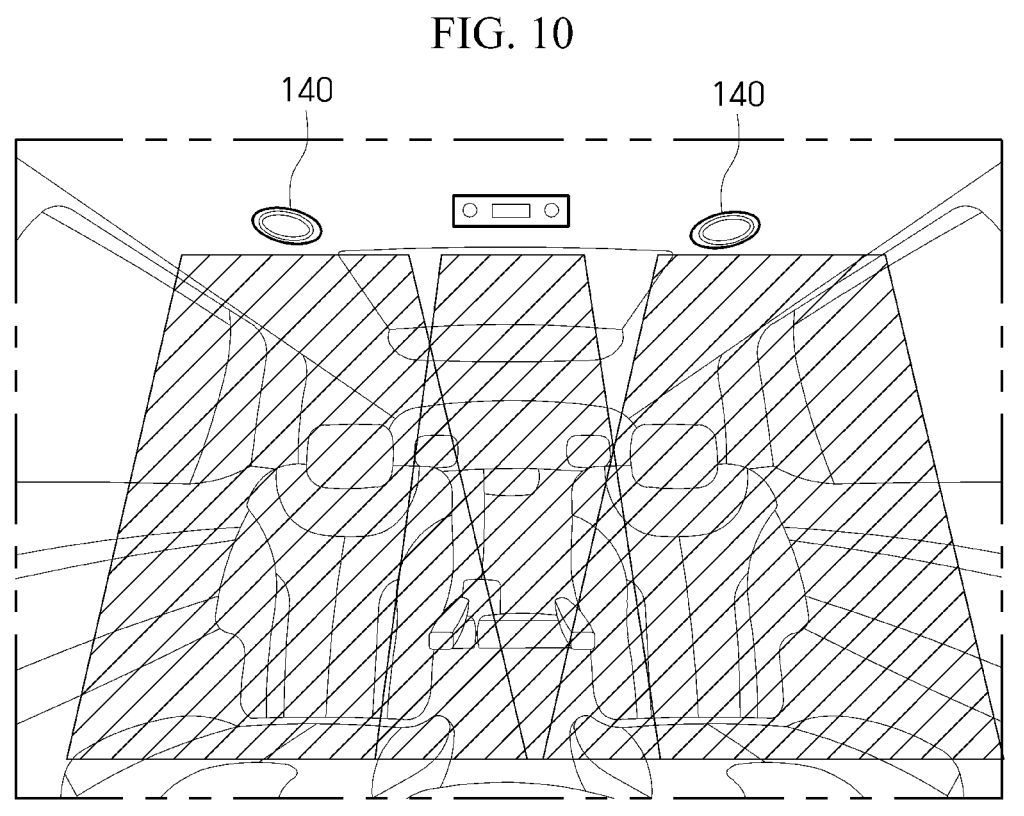

The sterilizing part 100 includes one or more ultraviolet light-emitting diodes (UV LEDs). The sterilizing part 100 may be provided together with a vehicle room lamp 110 illustrated in FIG. 2, a door lamp 120 illustrated in FIG. 7, or an ambient light (or mood lamp) 130 illustrated in FIG. 8. As illustrated in FIG. 9, the sterilizing part 100 may be disposed on a ceiling air vent 140 provided on the upper portion of the interior of a vehicle. The sterilizing parts 100 disposed on the ceiling air vents 140 provided on the upper portions of the interior of the vehicle serve to sterilize the entirety of the interior of the vehicle, as illustrated in FIG. 10.

Figure 2:
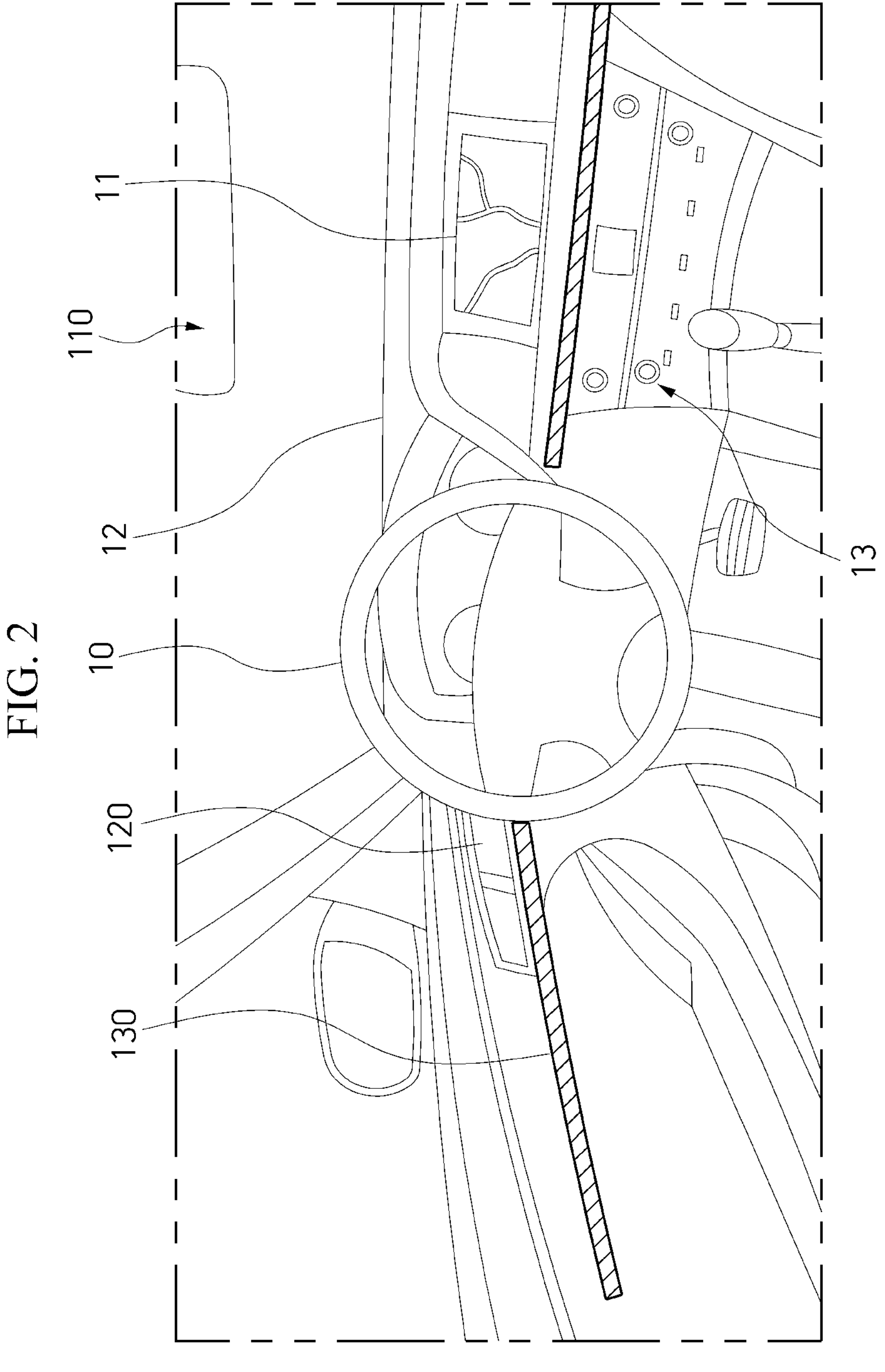
FIG. 2 is a reference view illustrating a room lamp on which the sterilizing part illustrated in FIG. 1 is disposed and objects to be sterilized by the sterilizing part.
Figure 3:
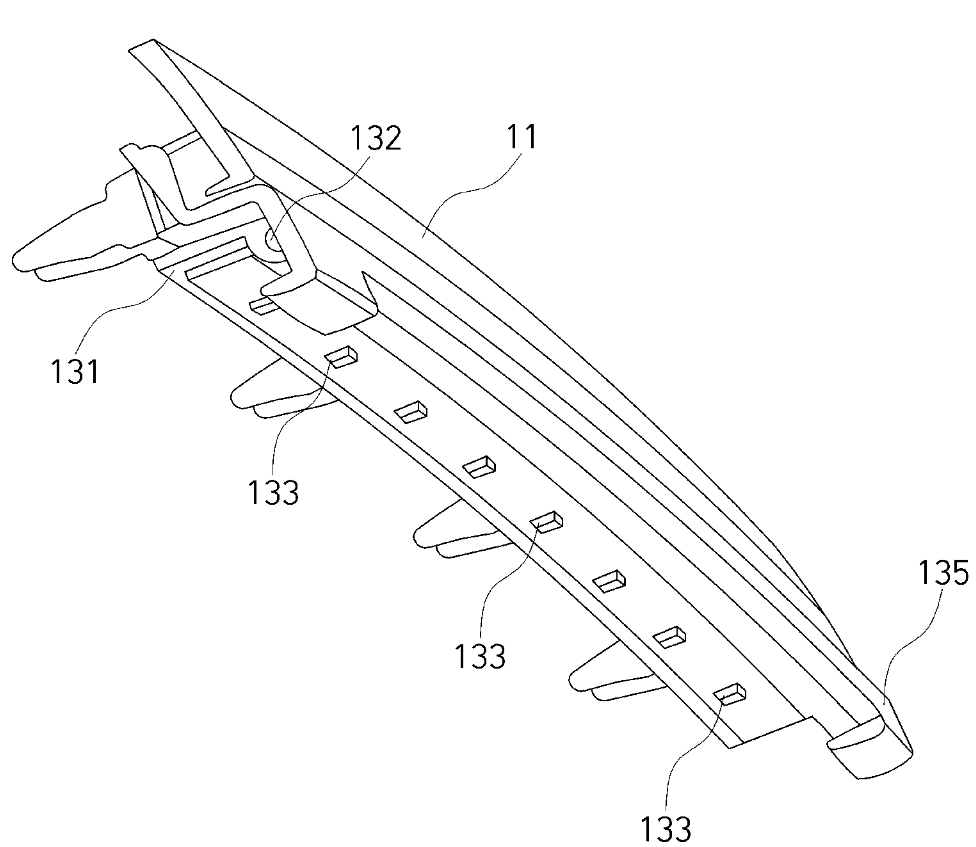
FIG. 3 is a perspective view of the sterilizing part illustrated in FIG. 1.
Figure 4:
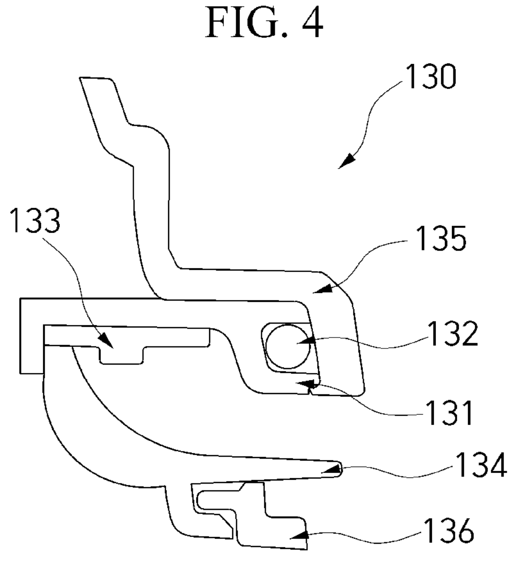
FIG. 4 is a side view of the sterilizing part illustrated in FIG. 1.
Figure 5:
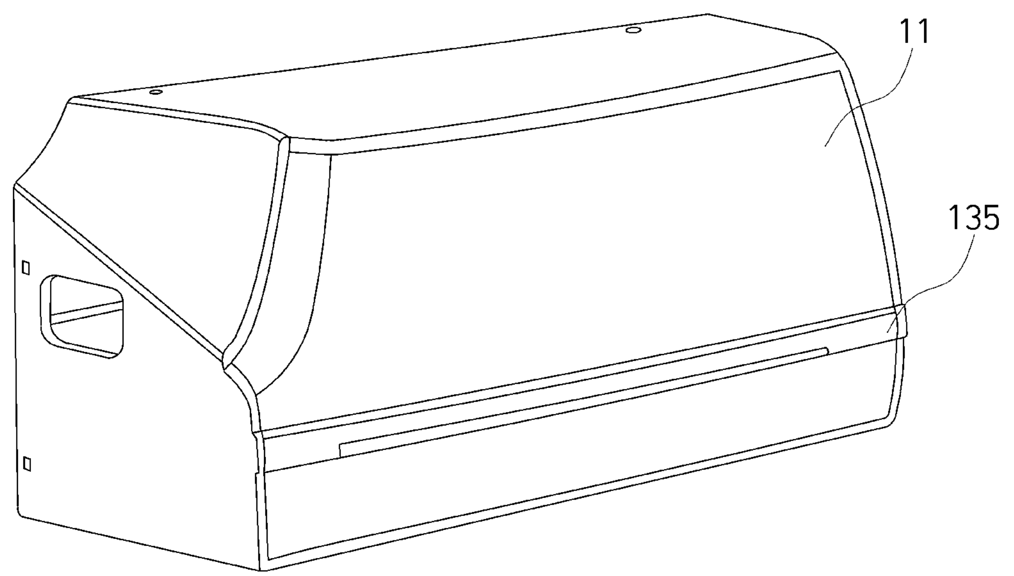
FIG. 5 is a reference view illustrating an example in which the sterilizing part illustrated in FIG. 1 is disposed on a dashboard.
Figure 6:
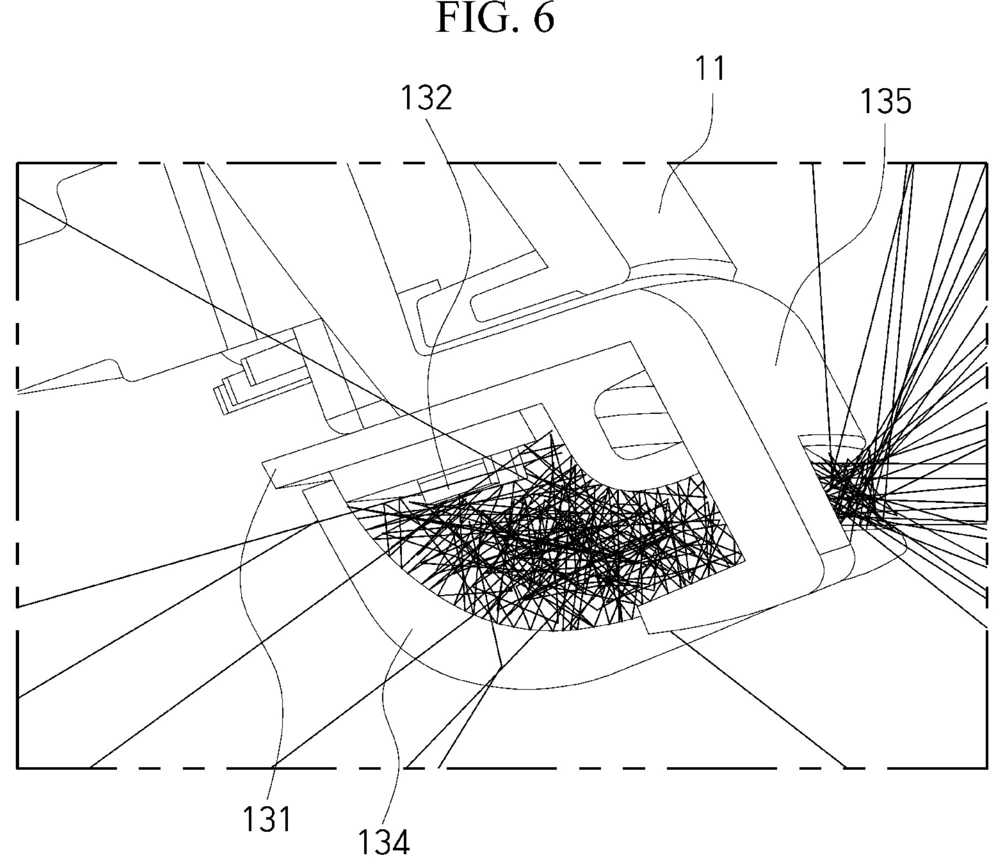
FIG. 6 is a reference view illustrating an example in which UV radiation by the sterilizing part illustrated in FIG. 1.

As illustrated in FIG. 2, the sterilizing part 100 disposed on the room lamp sterilizes a steering wheel 10, a dashboard 11, an audio, video, and navigation system (AVN) 12 disposed on the dashboard 11, an air conditioning system button 13, and a gearstick.

Meanwhile, as illustrated in FIGS. 3, 4, 5 and 6, the ambient light 130 in the sterilizing part 100 according to an embodiment of the present disclosure includes a housing 131, a luminescent fiber 132, UV LEDs 133, a UV reflector 134, an upper garnish 135, and a lower garnish 136.

The housing 131 is provided on a predetermined portion of the length of a door of the vehicle or a predetermined portion of the length of the dashboard 11. A channel having an open front portion is provided on a front portion of the housing 131 in the longitudinal direction, and the luminescent fiber 132 is seated in the channel. A UV mounting panel having a space for accommodating the UV LEDs 133 is provided below the rear portion of the channel. The UV LEDs 133 mounted on the lower portion of the UV mounting panel may be a plurality of UV LEDs arranged along the UV mounting panel. Meanwhile, according to another embodiment of the present disclosure, the housing 131 may be configured to accommodate the luminescent fiber 132 and the UV LEDs 133 without being provided with a separate channel in which the luminescent fiber 132 is disposed.

The UV reflector 134 is disposed below the UV mounting panel and spaced apart a predetermined distance from the housing 131, such that UV radiation generated by the UV LEDs 133 may be projected outward. The UV reflector 134 of the present embodiment may be configured to be curved so that UV radiation generated by the UV LEDs 133 may be projected in a variety of directions. Since the UV reflector 134 of the present embodiment is configured to be curved as described above, the UV radiation generated by the UV LEDs 133 may be uniformly projected to the interior of the vehicle. In addition, the range of projection of the UV radiation may be adjusted depending on the distance between the UV reflector 134 and the housing 131.

The upper garnish 135 covers an open portion of the channel such that the luminescent fiber 132 disposed in the channel of the housing is not dislodged outward. The upper garnish 135 according to the present embodiment may be formed of a material allowing light generated by the luminescent fiber 132 to pass therethrough and projected to the interior of the vehicle.

In addition, a UV transparent film may further be provided between the UV reflector 134 and the housing 131 to prevent external dust or the like from entering the interior.

Figure 7:
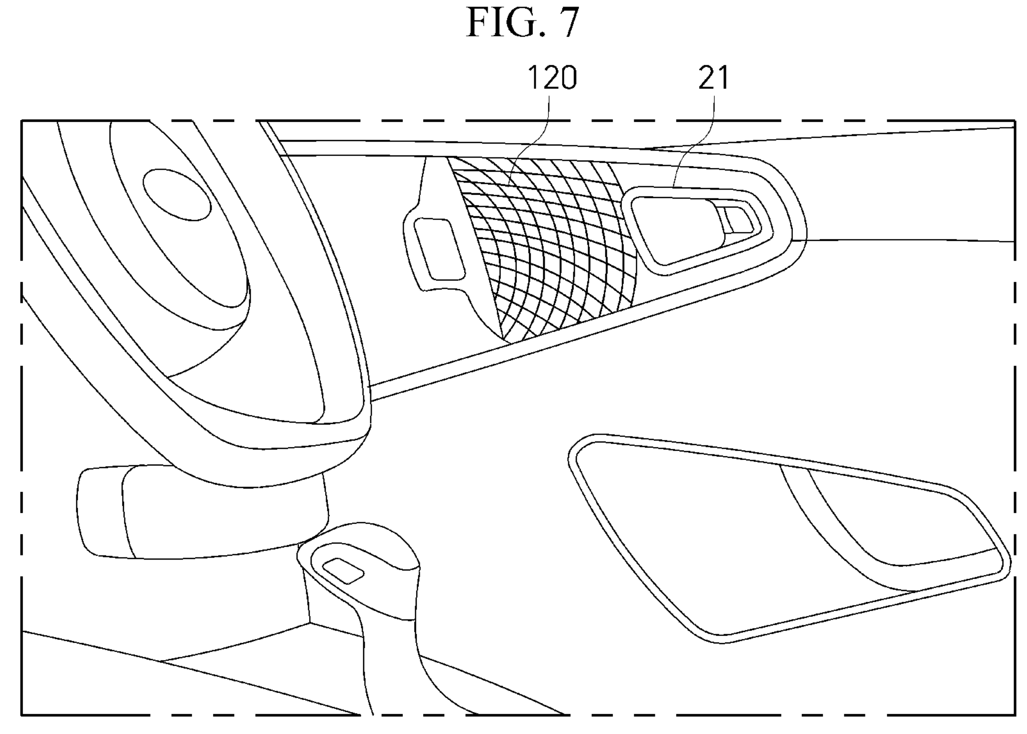
FIG. 7 is a reference view illustrating a door lamp on which the sterilizing part illustrated in FIG. 1 is disposed and objects to be sterilized by the sterilizing part.
Figure 8:
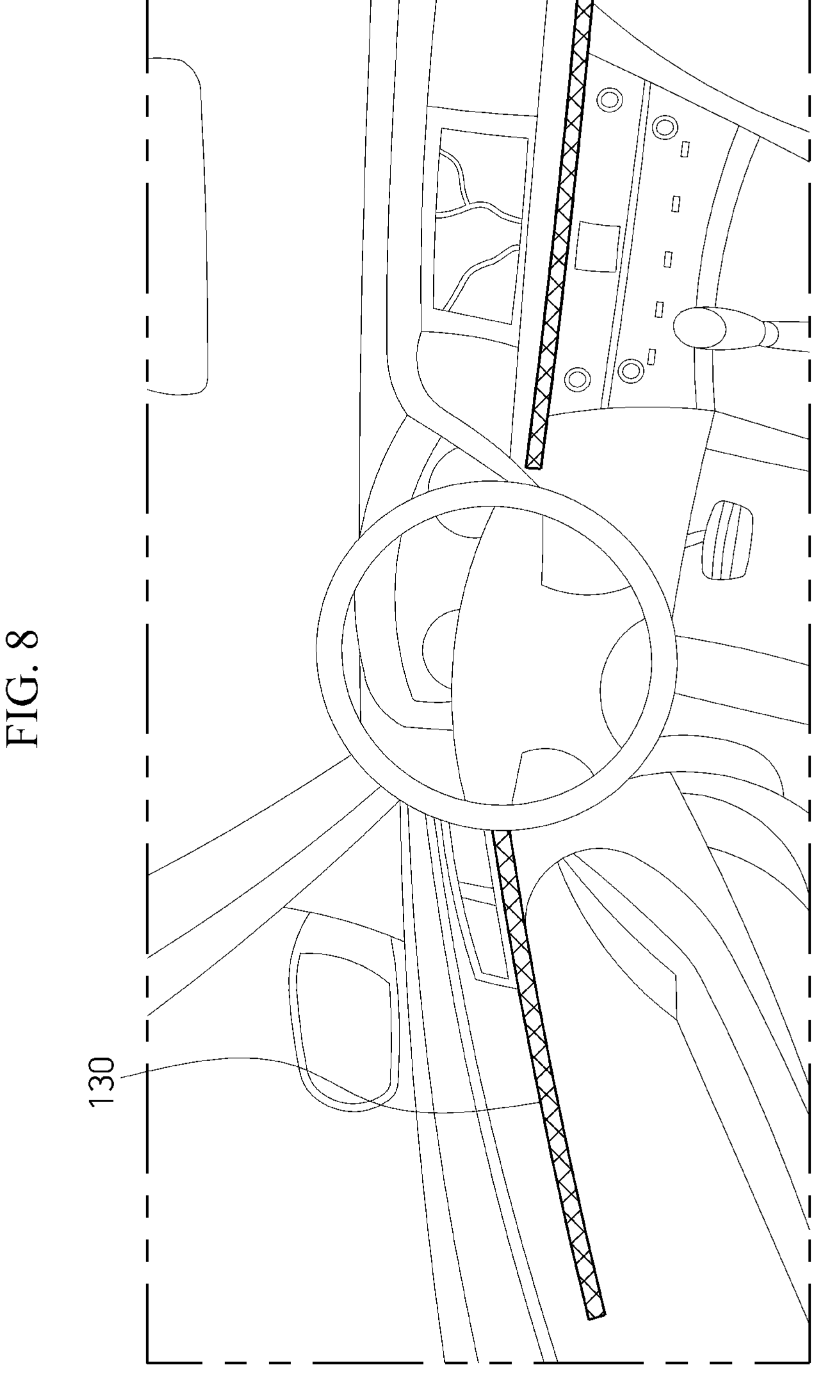
FIG. 8 is a reference view illustrating a mood lamp on which the sterilizing part illustrated in FIG. 1 is disposed and objects to be sterilized by the sterilizing part.

As illustrated in FIG. 7, the sterilizing part 100 disposed on the door lamp 120 sterilizes a door handle 21 inside the vehicle. As illustrated in FIG. 8, the sterilizing part 100 disposed on the ambient light 130 sterilizes the entirety of the interior of the vehicle.

The sterilization control part 200 controls the sterilizing part 100 so that the sterilizing part 100 is turned on or off depending on a result of the determination.

The driving determining part 300 determines a time point at which the sterilizing part 100 is to be operated. In this regard, the driving determining part 300 determines whether or not information regarding the operation time of the sterilizing part 100 set by the user is stored and, when the operation time is reached, controls the sterilization control part 200 so that the sterilizing part 100 operates during the operation time.

The communication part 400 receives a remote start signal and a remote sterilization request signal through communication with the remote control terminal 500. When the remote start signal and the remote sterilization request signal are received from the remote control terminal 500 through the communication part 400, the driving determining part 300 may instruct the sterilization control part 200 to control the sterilizing part 100 so that the sterilizing part 100 operates for a predetermined time. Here, the communication part 400 may use a communication protocol to transmit or receive a signal through radio frequency (RF) communication with the remote control terminal 500 provided as a vehicle smart key or may transmit or receive a signal through the Bluetooth communication protocol.

Figure 11:
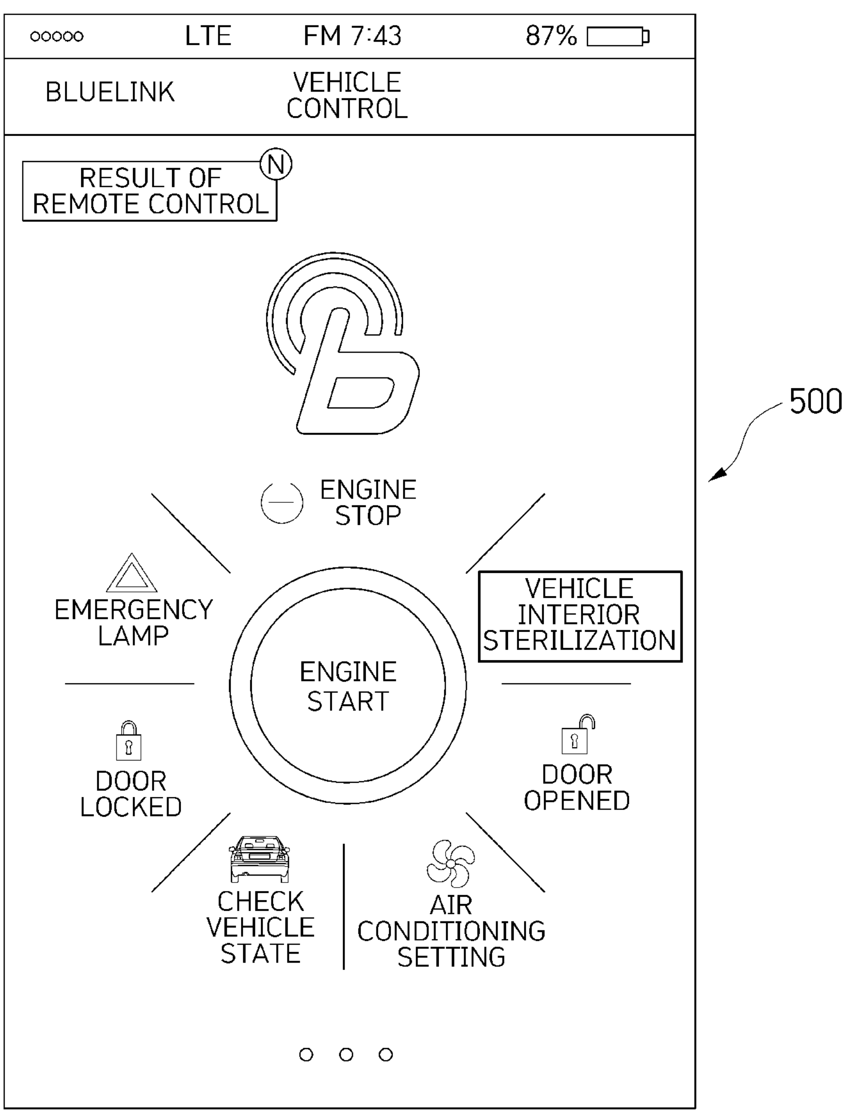
FIG. 11 is a reference view illustrating an example of a screen of the remote control terminal illustrated in FIG. 1.

Meanwhile, the remote control terminal 500 according to an embodiment of the present disclosure may be provided with a separate function of sterilizing the interior of the vehicle as an application is installed. A driver may transmit a remote start signal or a remote sterilization request signal to the vehicle through an application as illustrated in FIG. 11 when sterilization is desired (for example, is necessary, initiated, etc.). In addition, the remote control terminal 500 may control turning on/off of the UV lamp, turning on/off of the mood lamp, the color of the mood lamp, the brightness of illumination, and the like through the application.

The driving determining part 300 according to an embodiment of the present disclosure may be an electronic control unit (ECU) of the vehicle or may be implemented as an ECU of a separate AVN allowing services, such as remote control, safety security, vehicle management, and navigation, to be provided using a smartphone.

In addition, the communication part 400 may be implemented as a communication module of a terminal disposed in the vehicle to be started remotely by an application installed in the smartphone of the driver. The communication part 400 allows the vehicle to be identified by a separate universal subscriber identity module (USIM) card, and transmits or receives data to or from the smartphone of the driver through a mobile communication network.

Meanwhile, when unlocking of a locked door is detected during a predetermined driving time, the driving determining part 300 may control the sterilization control part 200 to end the operation of the sterilizing part 100.

This configuration may prevent the driver from being directly irradiated with harmful UV radiation when he/she gets in the vehicle while the sterilizing part 100 is being driven.

In addition, a sterilization request is input by the remote control terminal, the driving determining part 300 may control the sterilization control part 200 to operate in one of a quick sterilization mode in which only some of a plurality of sterilizing parts 100 operate an entirety sterilization mode and in which the entirety of the sterilizing parts 100 are operated according to the setting of the vehicle itself. Meanwhile, the driving determining part 300 may further include a sensing part detecting whether or not a child or a pet is inside the vehicle when the sterilization request is input by the remote control terminal. The sensing part may include one or more sensors selected among a camera sensor, a temperature sensor, and $CO_2$ sensor.

Thus, when the sterilization request is received from the remote control terminal, the driving determining part 300 may operate the sensing part to detect whether or not a child or a pet is inside the vehicle and, when detecting the child or the pet inside the vehicle, controls the sterilizing part 100 not to operate.

According to the present embodiment, when the driving of a vehicle is stopped in the dawn after the vehicle is parked or an electric vehicle is being charged, a sterilization diagnosis function may be performed. In addition, during commuting in weekdays, the entirety sterilization mode may be performed when the entirety sterilization mode is set according to the setting of the vehicle itself, or the quick sterilization mode may be performed when sterilization is requested at an unspecified time and in an unspecified place.

Figure 12:
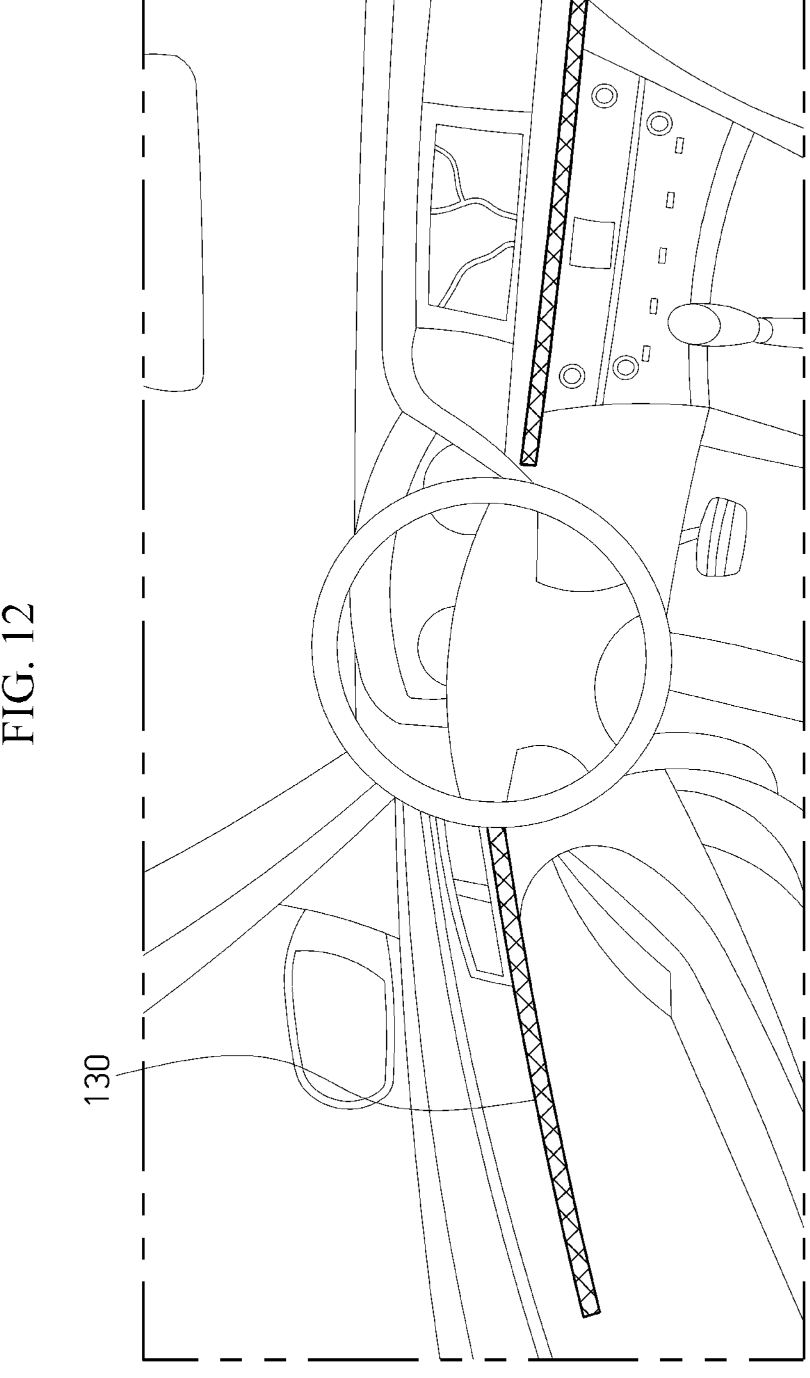
FIG. 12 is a reference view illustrating an example color of illumination in the operation of the sterilizing part according to an embodiment of the present disclosure.
Figure 13:
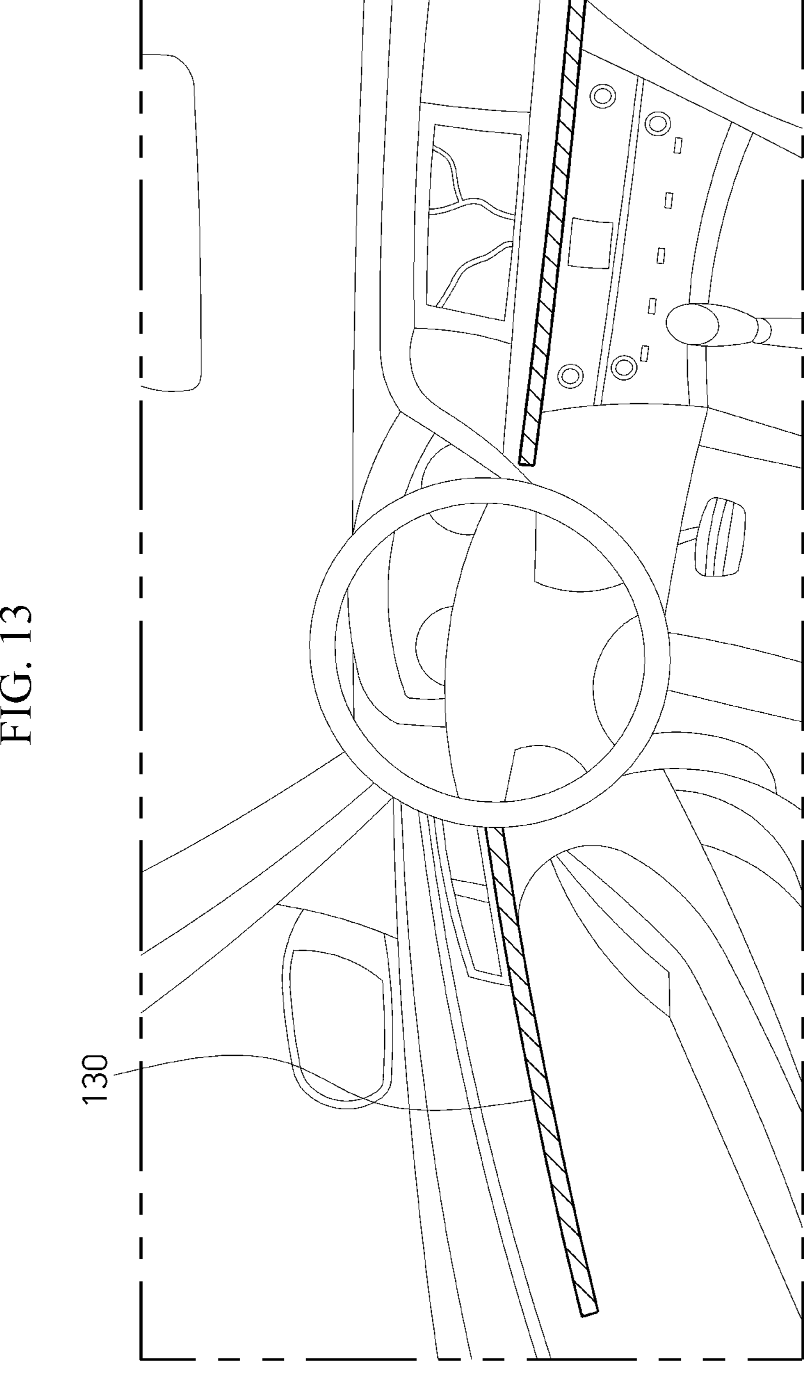
FIG. 13 is a reference view illustrating an example color of illumination after the operation of the sterilizing part according to an embodiment of the present disclosure is completed.

Meanwhile, the sterilizing part 100 operates simultaneously with an LED lamp having a visible light wavelength range. The LED lamp is operated by changing the color depending on the operation of the sterilizing part 100. For example, when the sterilizing part 100 is operating, the ambient light (or mood lamp) is operated to project purple light or red light to notify that the sterilizing part 100 is operating as illustrated in FIG. 12. When the operation of the sterilizing part 100 is ended due to the completion of the sterilization of the interior of the vehicle, the ambient light is operated to project green light to notify the occupant of the completion of the sterilization as illustrated in FIG. 13. Thus, an accident in which the occupant is directly irradiated with UV radiation projected form the sterilizing part may be prevented.

Meanwhile, the driving determining part 300 determines the operation mode on the basis of a time point and a position at which the sterilization of the interior of the vehicle is requested and a driver use pattern.

For example, in a situation in which doors are locked after the driver ends the driving of the vehicle, when a signal regarding the function of sterilizing the interior of the vehicle is received from the remote control terminal 500 through the communication part 400, the driving determining part 300 determines the quick sterilization mode to be activated.

In contrast, when the vehicle is determined to be in a parking state after the driver ends the driving of the vehicle, the driving determining part 300 determines the entirety sterilization mode to be activated. For example, after the driving of the vehicle is ended, when a predetermined time has passed, the driving determining part 300 may determine the vehicle is in a parking state, and thus activate the entirety sterilization mode. When the vehicle is parked in a designated position, i.e., the resident of the driver, the driving determining part 300 may determine the entirety sterilization mode to be activated.

The operation mode according to the present embodiment includes the quick sterilization mode in which only some of the sterilizing parts 100 operate and the entirety sterilization mode in which the entirety of the sterilizing parts 100 provided inside the vehicle operate.

Meanwhile, the sterilizing part 100 may be disposed on at least one of the mood lamp, the door lamp, and the room lamp. The sterilizing part 100 disposed in this manner operates when the quick sterilization mode is activated. In general, the sterilizing part 100 concentrically sterilizes a location on the steering wheel or the door switch to be frequently in contact with a pollutant, such as the driver.

In addition, the sterilizing part 100 may be provided on an air vent in an air conditioning system provided in the ceiling inside the vehicle. When the sterilizing part 100 is provided on the air vent in an air conditioning system provided in the ceiling inside the vehicle, the sterilizing part 100 may be operated in the entirety sterilization mode.

The term "part" used in this specification may include a unit implemented as hardware, software or firmware, and may be interchangeably used with a term, such as logic, a logical block, a unit, or a circuit. The "part" may be an integrated part, or a minimum unit of the part or a part thereof, which performs one or more functions. For example, according to an embodiment, the "part" may be implemented in the form of an application-specific integrated circuit (ASIC). Furthermore, an implementation described in this specification may be realized as a method or process, an apparatus, a software program, a data stream or a signal, for example. Although the present disclosure has been discussed only in the context of a single form of an implementation (e.g., discussed as only a method), an implementation having a discussed characteristic may also be realized in another form (e.g., apparatus or program). The apparatus may be implemented as proper hardware, software or firmware. The method may be implemented in an apparatus, such as a processor commonly referring to a processing device, including a computer, a microprocessor, an integrated circuit or a programmable logic device, for example. The processor includes a communication device, such as a computer, a cell phone, a mobile phone/personal digital assistant ("PDN") and another device which facilitates the communication of information between end-users.

Examples of the present disclosure may provide an effect capable of removing harmful microorganisms and viruses present inside a vehicle by sterilizing the interior of the vehicle in any conditions.

Various embodiments provide for performance of automatic in-vehicle sterilization using an application, such as Bluelink, installed in the smartphone of the driver prior to the driver entering (or operating) the vehicle. When embodiments are used in public transportation means, such as a sharing car, a taxi, a bus, and a subway, used by unspecified people, an effect of restricting the spread of virus may be obtained.

In addition, according to an embodiment of the present disclosure, it is possible to realize a hybrid function using a variety of available lamps (e.g., room lamps and door lamps) in a vehicle and a ceiling air conditioning system.

Respective descriptions of the various embodiments of the present disclosure do not itemize all available combinations, and descriptions of various embodiments may be applied independently or may be applied through a combination of two or more. Features of an embodiment may be applicable to any other embodiment or combination of embodiments.

Moreover, various embodiments of the present disclosure may be implemented with hardware, firmware, software, or a combination thereof. In a case where various embodiments of the present disclosure are implemented with hardware, various embodiments of the present disclosure may be implemented with one or more application specific integrated circuits (ASICs), digital signal processors (DSPs), digital signal processing devices (DSPDs), programmable logic devices (PLDs), field programmable gate arrays (FPGAs), general processors, controllers, microcontrollers, or microprocessors.

The scope of the present disclosure may include software or machine-executable instructions (for example, an operation system (OS), applications, firmware, programs, etc.), which enable operations of a method according to various embodiments to be executed in a device or a computer, and a non-transitory computer-readable medium capable of being executed in a device or a computer each storing the software or the instructions.

A number of embodiments have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An in-vehicle sterilization system for a vehicle, the in-vehicle sterilization system comprising:

a sterilizer comprising one or more ultraviolet (UV) light-emitting diodes (LEDs) and an LED lamp; and one or more processors configured to:

determine a time point at which the sterilizer is to be operated;

control operation of the sterilizer according to a result of the determination; and control the LED lamp by changing colors depending on whether or not the sterilizer operates, wherein the sterilizer further comprises:

a housing comprising a longitudinal channel provided on a front portion of the housing and having an open front portion and a UV mounting panel provided below a rear portion of the channel and having a space for accommodating the UV LEDs;

a luminescent fiber disposed in the channel of the housing to project RGB light under control; and an upper garnish configured to cover an open portion of the channel such that the luminescent fiber disposed in the channel is not released outward, and wherein the UV LEDs are mounted on a lower portion of the UV mounting panel to generate UV radiation under control.

2. The in-vehicle sterilization system of claim 1, wherein the one or more processors are further configured to:

determine whether or not information regarding the operation time of the sterilizer is stored; and when the operation time is reached, control operation of the sterilizer for the operation time.

3. The in-vehicle sterilization system of claim 1, further comprising:

a communication part, including a first transceiver, configured to communicate with a remote including a second transceiver, wherein, in response to a remote start signal and a remote sterilization request signal are received through the communication part, the one or more processors are further configured to control operation of the sterilizer for the operation time.

4. The in-vehicle sterilization system of claim 3, wherein, in response to unlocking of a door is detected during the operation time, the one or more processors are further configured to stop the control operation of the sterilizer.

5. The in-vehicle sterilization system of claim 3, wherein the sterilizer further comprises a plurality of sterilizing components, and wherein, in response to a sterilization request being received from the remote, the one or more processors are further configured to operate the sterilizer, according to setting of a vehicle itself, in one of:

a quick sterilization mode in which at least some of the plurality of sterilizing components operate, and an entirety sterilization mode in which all of the plurality of sterilizing components operate.

6. The in-vehicle sterilization system of claim 5, further comprising:

at least one sensor configured to detect whether one or more of a child or a pet is present inside the vehicle, wherein, in response to the sterilization request being received from the remote control terminal, the one or more processors are further configured to detect whether a child or a pet is present inside the vehicle and, wherein, in response to a determination that neither the child nor the pet present inside the vehicle, the one or more processors are further configured to operate the sterilizer.

7. The in-vehicle sterilization system of claim 1, wherein the UV LEDs are a plurality of UV LEDs arranged along the UV mounting panel.

8. The in-vehicle sterilization system of claim 1, further comprising a UV reflector disposed below the UV mounting panel and at a predetermined distance from the housing such that the UV radiation generated by the UV LEDs is projected outward.

9. The in-vehicle sterilization system of claim 8, wherein the UV reflector has a predetermined curvature so that the UV radiation generated by the UV LEDs is uniformly projected.

10. The in-vehicle sterilization system of claim 9, further comprising a UV transparent film between the UV reflector and the housing.

11. The in-vehicle sterilization system of claim 1, wherein the sterilizer further comprises a plurality of sterilizing components disposed on one or more of a mood lamp, a door lamp, and a room lamp.

12. The in-vehicle sterilization system of claim 1, wherein the sterilizer is disposed on an air vent of an air conditioning system provided in a ceiling of a vehicle.

13. The in-vehicle sterilization system of claim 1, wherein information regarding a result of the operation of the sterilizer is transmitted to and displayed on an audio, video, and navigation (AVN) system or a remote control terminal.

* * * * *